United States Patent [19]

Härdmark

[11] 4,212,063
[45] Jul. 8, 1980

[54] APPARATUS FOR MEASURING THE ACTION OF FORCES BETWEEN WHEELED VEHICLES AND SUBSTRUCTURE

[75] Inventor: Ragnar M. Härdmark, Linköping, Sweden

[73] Assignee: Saab-Scania Aktiebolag, Sodertalje, Sweden

[21] Appl. No.: 940,038

[22] Filed: Sep. 6, 1978

[51] Int. Cl.² .......................................... G01N 19/02
[52] U.S. Cl. ........................................ 364/426; 73/9;
73/128; 364/424; 364/565
[58] Field of Search .............. 364/426, 424, 425, 565;
73/1 R, 1 B, 1 C, 8, 9, 128, 129; 324/16 R, 160,
161; 235/95 R, 96, 92 DN

[56] References Cited

U.S. PATENT DOCUMENTS

| | | | |
|---|---|---|---|
| 3,362,757 | 1/1968 | Marcheron | 73/129 |
| 3,846,701 | 11/1974 | Sampey | 235/92 DN |
| 3,893,330 | 7/1975 | Shute et al. | 73/9 |
| 4,067,061 | 1/1978 | Juhasz | 364/424 |
| 4,098,111 | 7/1978 | Hardmärk et al. | 73/9 |
| 4,130,008 | 12/1978 | Broshears | 73/9 |

Primary Examiner—Errol A. Krass
Attorney, Agent, or Firm—Cushman, Darby & Cushman

[57] ABSTRACT

An apparatus for measuring the action of forces between a wheeled vehicle and a substructure wherein the invention relates to the improvement of a measuring apparatus having a plurality of controls for selecting measuring distances of varying lengths, with each control programmed to trigger, when actuated, a memory in an electronic unit arranged to compare a signal value preselected to represent the measuring distance with a signal value generated by summing up output signals from a vehicle speed transducer and wherein the electronic unit is programmed to trigger discontinuation of the measuring sequence when the two signal values are equal which will be obtained at the end of the measuring distance.

9 Claims, 5 Drawing Figures

APPARATUS FOR MEASURING THE ACTION OF FORCES BETWEEN WHEELED VEHICLES AND SUBSTRUCTURE

BACKGROUND OF THE INVENTION

The present invention relates to a measuring apparatus incorporated in a motor vehicle which measures and indicates the relevant limiting values for driving and braking vehicles on a prevailing substructure (e.g., roadways and runways). This invention is an improvement of the art disclosed in applicant's U.S. application Ser. No. 763,081, filed Jan. 27, 1977 now U.S. Pat. No. 4,098,111.

In vehicles provided with a measuring wheel and instrumental equipment for making measurements on airport runways it has usually been difficult for a solitary driver of a measuring vehicle to both drive the vehicle and make the measurements. This has often resulted in the nullification of the value of such measurements due to faulty operation. As a result of the desire to reduce this kind of risk, it is usual for a measuring vehicle to have a crew of two—a driver and a technician for the measuring equipment. Even this, however, does not guarantee that measured values will be correct, since the measurements are generally taken via the manual operation of controls triggering activation and deactivation of measuring functions.

The purpose of the present invention is to provide a measuring apparatus integrated in a motor vehicle, for measuring road and/or runway properties to give vehicles moving at high speeds an optimum retardation on a prevailing substructure. Another object of this invention is to provide a measuring apparatus capable of providing correct measured value and capable of being operated solely by a driver. Other objects will become apparent from the following detailed description.

SUMMARY OF THE INVENTION

The present invention relates to a measuring apparatus which is incorporated in a motor vehicle, to a large extent enabling automatic measuring methods, and is especially advantageous for measurements on airport runways. The measuring apparatus comprises at least one measuring wheel rotatably mounted in the vehicle, said wheel being adapted for engaging the substructure, at least during measuring operations, and for rotation with an amount of slip in relation to the speed of the wheeled vehicle; at least one control panel arranged in the vehicle, with a plurality of control means, e.g., push buttons or keys, for control and selection of a measuring sequence; at least one measuring transducer for sensing the forces and/or torque acting on the measuring wheel and generating signals corresponding thereto; at least one measuring transducer for sensing the speed of the vehicle and generating a pulsed signal corresponding thereto; and at least one electronic unit mounted in the vehicle, for receiving and processing signals generated by the transducers, and in response thereto transmitting output signals to a plurality of instruments displaying the measuring result; the invention being mainly distinguished in that the control panel comprises a plurality of controls for selecting measuring distances of different length; each such control being arranged to trigger, when actuated, the switching in circuit of a signal value preselected to represent the measuring distance in question in a memory or the like incorporated in the electronic unit; said electronic unit being arranged to compare said signal value with a signal value generated by summing up the signal pulses from the vehicle speed transducer and representing the distance travelled by the vehicle during a measuring sequence, said electronic unit also being arranged to trigger discontinuation of the measuring sequence in question when equal signal values are obtained.

Such said equality of signal values is intended to be attained at the end of a preselected measuring distance, whereby a signal is applied to a circuit, which in turn is arranged to activate servo means to raise the measuring wheel from the substructure to an inactive position.

The entire scope of the present invention will become apparent from the following description and reference to the accompanying drawings. It should be understood, however, that the description and the specific examples while indicating preferred embodiments, are given by way of illustration only, since various changes and modifications within the spirit and scope of the invention will become apparent as the description herein progresses.

Figure 1:
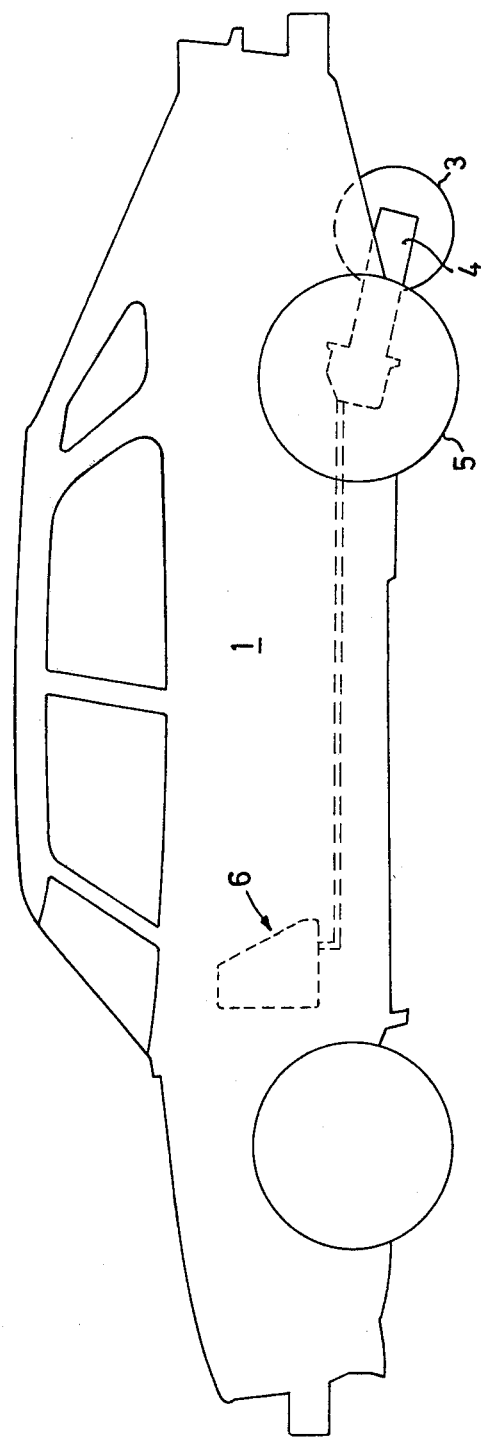
FIG. 1 shows a schematical side view of a measuring wheel arrangement according to the invention, installed in the rear of an automobile.

In one embodiment of a measuring wheel arrangement, exemplified in FIG. 1, a measuring wheel 3 is built into an automobile 1 and placed half-way between the rear wheels 5 of the automobile 1. The measuring wheel 3 is pivotable mounted in the automobile 1 in a vertical plane and in FIG. 1 the measuring wheel 3 is showed in a position ready for measurement. The measuring wheel 3 is in driving force transmitting communication with the rear wheels 5 of the automobile 1 by means of a transmission 4. The transmission 4 is so selected that the measuring wheel 3 has a reduced rotational speed in relation to the rotational speed corresponding to free rolling. The loads acting upon the measuring wheel 3 are measured by strain gauges (not shown). The signals from the strain gauges are led to an electronic unit 6, which in this embodiment is placed near the driver's seat.

Figure 2:
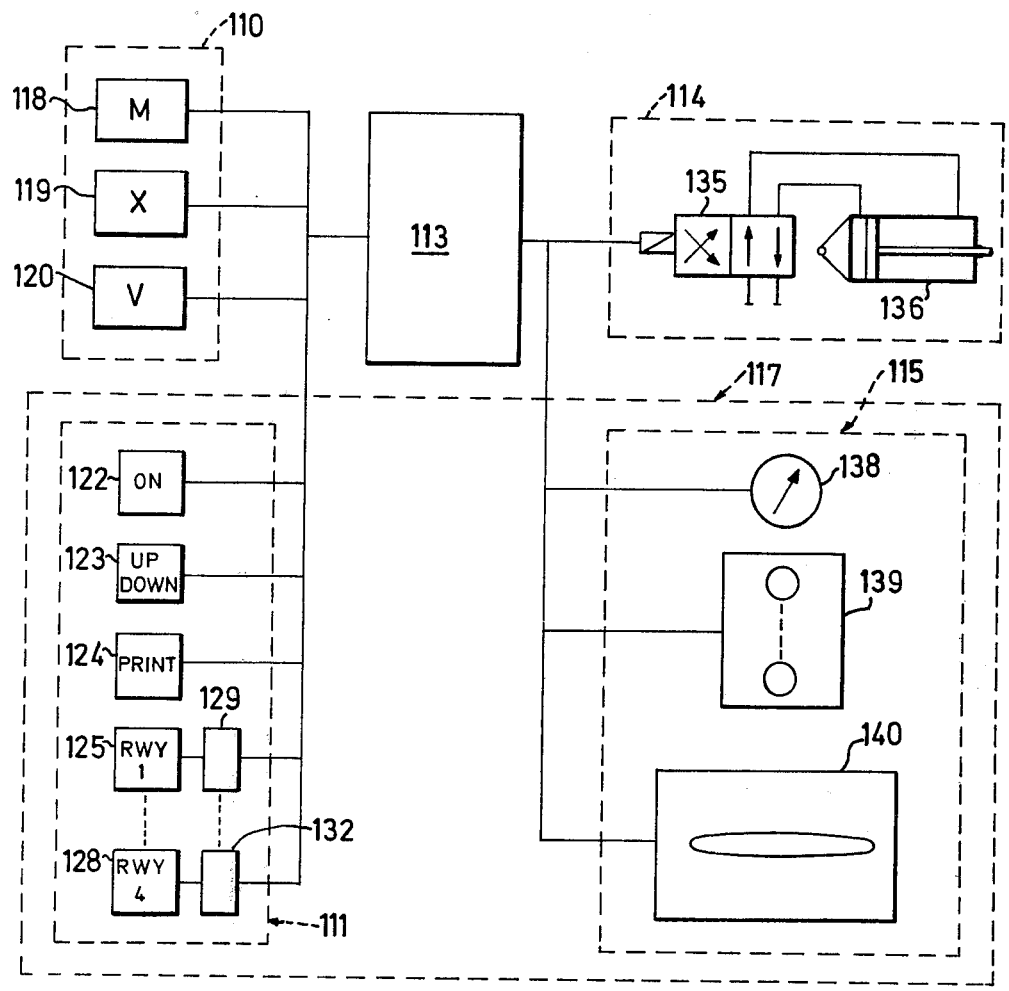
FIG. 2 shows a block diagram of the electrical system pertaining to the measuring apparatus, FIG. 3 schematically illustrates signal processing in the electronic unit.

FIG. 2 illustrates how measuring transducers in the measuring equipment and controls included in a control panel are arranged to coact with a plurality of instruments and servocontrols via the electronic unit, in the following called the central block 113. With relation hereto, the measuring equipment is differentiated into a plurality of function related blocks. For description, the measuring transducers are collected in a transducer block 110, and the operating controls at the driver's seat are collected in a control block 111. Controls and transducers in the respective blocks 111, 110 are arranged to transmit input signals to the central block 113 via separate lines. Said central block 113 processes the input signals and transmits output signals to a block 114, controlling servocontrols for raising and lowering the measuring wheel 3, and also to a block 115 for analog and- /or digital registration of measuring results. The control block 111 and the registration block 115 are suitably arranged in a control and registering unit 117, comprising a control panel adjacent the driver's seat and within his easy reach.

In the transducer block 110 there are a plurality of signal-generating transducers 118,119,120, denoted by M, X, and V, respectively, in FIG. 2. The transducer 118 senses by means of a chain tensioner (not shown) torque acting on the wheel 3, said torque being proportional to a friction force acting on the wheel 3. The transducer 119 senses horizontal forces acting on the wheel 3, these forces being sensed by means of a hub transducer (not shown). The transducer 120 senses the vehicle speed. Signals representing the vehicle speed are generated in a conventional manner, by a pick-up coacting with a toothed wheel rigidly attached to one of the ordinary wheels of the vehicle. In the embodiment of the measuring equipment electrical system exemplified in FIG. 2, vertical forces acting on the wheel 3 are pre-programmed as a constant factor in the electronic unit. It means that the value of the friction coefficient $\mu$ then becoming directly dependent on the measured value of the tensional force acting on the wheel 3.

The operating control block 111 comprises a plurality of switches, having the following functions, in order. The switch 122, denoted ON, controls the current supply to the measuring equipment. The switch 123, denoted UP/DOWN, is a toggle switch controlling raising and lowering of the wheel 3 relating to the substructure. For the position UP, the wheel 3 is raised to a position retracted against the automobile 1, while for the position DOWN, the wheel 3 is lowered into engagement with the substructure. The switch 124, denoted PRINT, triggers pre-programmed signal processing in the central block 113, and also triggers a chart recorder 140 in the registration block 115 to start registering data obtained from the central block 113.

The switches 125–128, denoted RWY1–RWY4 are controls for selecting four different measuring distance alternatives, and RWY is a shortened form of "runway". The length of each measuring distance can be preset by adjusting a voltage level on the respective potentiometer 129–132, intended for this purpose (similar components for variably setting threshold values for measuring signals can, of course, be used).

Further, to said switches 122–128, more switches with controlling functions for other measuring sequences than those exemplified in FIG. 2 can be incorporated in the control block 111.

As previously mentioned, the block 114 is arranged to control movement of the wheel 3 between its downward and upward positions. An output signal from the central block 113 hereby actuates a solenoid valve 135 to regulate the flow of hydraulic fluid to and from both chambers of a hydraulic cylinder 136. When the piston rod of the cylinder 136 is displaced, the wheel 3 is swung via an angled crank and cable (not shown).

An indicating instrument 138, a lamp unit 139, comprising signal lamps, and said chart recorder 140 are included in the registration block 115. The instrument 138 indicates the momentary friction valve during a measuring sequence, and the signal lamps in the lamp unit 139 are arranged to indicate different conditions, e.g., lowered measuring wheel 3, selected measuring distance, current supply to the electrical system, etc. The chart recorder 140 gives in curve form on a chart an analog representation of the momentary friction value. At the same time, there is also digitally shown on the chart average values calculated in the central block 113 for measured frictional conditions and roll resistance, as well as other data for determining the condition of a runway or highway.

At the beginning of a measuring sequence it is necessary for the driver to first start the vehicle engine (not shown) before he can switch on the measuring apparatus electrical system by pressing the ON button 122. A lighted lamp on the lamp unit 139 indicates that the measuring apparatus is in circuit. The automobile 1 is then accelerated to a suitable speed for carrying out measurements, the driver meanwhile selecting a measuring distance by depressing one of the four RWY buttons 125–128. The wheel 3 is then lowered to measuring position by putting the UP-DOWN SWITCH 123 into the DOWN position, indicated by a lamp in the lamp unit 139. Finally, the PRINT button 124 is depressed, which starts signal processing in the central block 113.

Figure 3:
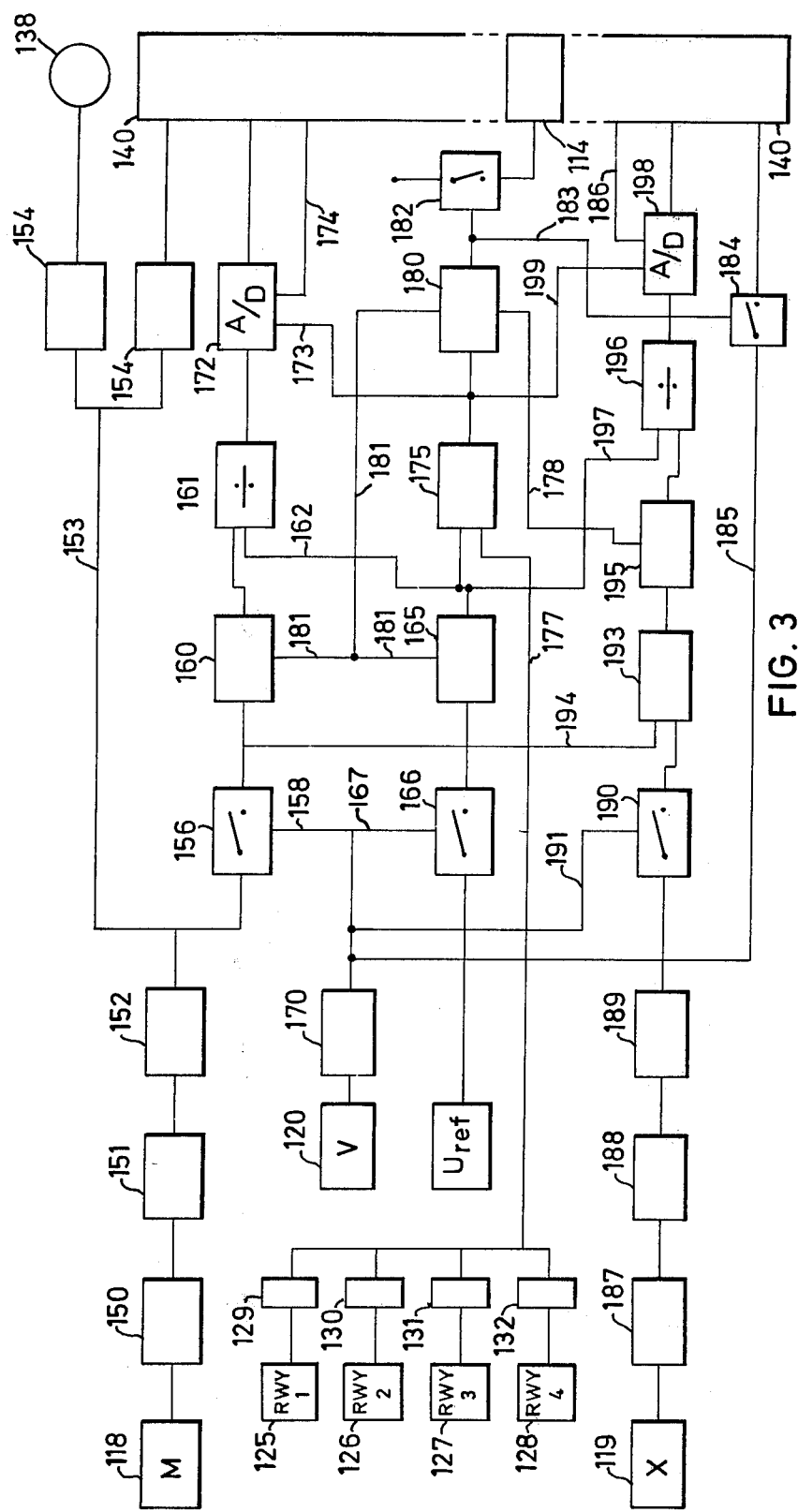

Such signal processing in the central block 113 is illustrated in FIG. 3. A signal transmitted by the torque transducer 118 is amplified in a differential amplifier 150, a low-pass filter 151 being used to filter out high-frequency noise and the like, before the signal is further amplified in an amplifier 152. The signal represents the torque acting on the wheel 3, and providing a vertical load on the wheel 3 is programmed in as a constant factor in the central block 113, the signal also represents the friction coefficient $\mu$ for the substructure.

The output signal from the amplifier 152 is taken (i) via a line 153 to two final amplifiers 154, connected in parallel, for output in analog form on the indicating instrument 138 and the chart recorder 140, and (ii) also to a sampling circuit comprising a switch 156 for opening and closing signal throughput in response to pulsed control signals in a line 158. A pulsed signal with an amplitude proportional to the $\mu$ value is thereby obtained after the switch 156. This signal is taken further to an integrator 160, on the output of which there is obtained a signal value representing the integrated pulses. Said output signal is taken to a divider circuit 161 and is there divided by a signal which is fed into the divider circuit 161 via a line 162.

The line 162 is connected to the output of an integrator 165. The signal on the output of the integrator 165 is the result of an integration of signal pulses from a switch 166, to which there is fed a signal from a reference voltage source $U_{ref}$. The switch 166 opens or blocks signal throughput in response to pulsed control signals in a line 167. Said control signals as well as the control signals in the line 158 are transmitted from a pulse shaper 170, which converts a speed signal V received from the transducer 120 into pulses. The number of pulses constitutes a direct measure of the distance travelled by the automobile 2 during the measuring sequence.

The common control signal to the switches 156, 166 results in their opening and closing times being identical. The output signal from the integrator 160 will represent the sum of signal pulses of different magnitudes, representing $\mu$ during a predetermined time and measuring distance. In the same way, the output signal from the integrator 165 will represent the sum of signal pulses having a constant value during exactly the same time and distance. The division of said summed-up signals in the divider circuit 161 thus gives an output signal representing an average value of the friction over a preselected time and distance. Said output signal is applied to an A/D-converter 172 (analog/digital-converter), for converting the analog input signal to a digital output signal in response to a control signal in a line 173. After conversion, a control signal is transmitted to the chart recorder 140 via a line 174, thereby triggering a permanent digital registration of the average frictional coefficient over the distance in question on a tape or the like.

The control signal in the line 173 is transmitted by a comparator 175 arranged to provide a high output signal level when a pre-selected distance has been travelled. This is achieved by applying to the comparator 175 the output signal from the integrator 165, representing the distance travelled by the automobile 1 during a measuring sequence, and a signal from the control block 111 via a line 177, this signal having a constant value representing a preselected measuring distance. The measuring distance is one of several alternatives, in this case four, which can be individually selected by operating the RWY switches 125–128, shown in FIG. 2. The respective signal values at the switches 125–128, corresponding to the measuring distances, are adjustable by means of the respective potentiometer 129–132, each provided with a scale (not shown). When such a selected value is exceeded by the value of the output signal from the integrator 165, the comparator 175 transmits said high level output signal.

The output signal from the comparator 175 is also transmitted to a counter 180. A delaying circuit in the latter causes the output signal to have a certain lag relative to the moment of change-over for the comparator, the output signal being transmitted via a line 181 to the integrators 160, 165 for zeroing them. These integrators then assume the starting condition for a new integration, to calculate average values for the friction conditions of the next measuring distance.

There is also a circuit in the counter 180 which, when the comparator 175 has thrice assumed a higher output signal level, transmits an output signal to a switch 182 in the circuit controlling the solenoid valve 135 in the block 114 for swinging the wheel 3. When there is an output signal from the counter 180, the switch 182 is operated causing the wheel 3 to be swung up from engagement with the substructure to an inactive position against the automobile 1.

The output signal from the counter 180 is also transmitted via a line 183 to a switch 184 in a line 185 between the pulse shaper 170 and the chart recorder 140. The recorder is supplied with a pulsed current via the line 185, giving the information carrier, e.g., a tape, a speed proportional to the vehicle speed V. When the counter 180 transmits an output signal, the switch 184 breaks the current to the recorder motor, thereby stopping propulsion of the tape and registration of data on it.

FIG. 3 also illustrates how signals from the X-transducer 119 are processed in the central block 113. Processing agrees in general with that described above for signals from the M-transducer 118. After amplification in an amplifier 187, filtering in a low-pass filter 188 and further amplification in an amplifier 189, the X-signal is applied to a switch 190, which for signal throughput is controlled by signal pulses from the pulse shaper 170, via a line 191. Analogously with the earlier description, this means that the switch 190 is controlled by signal pulses having a frequency directly proportional to the vehicle speed and that the number of pulses corresponds to the distance travelled by the vehicle during a measuring sequence.

The pulsed X-signal on the output of the switch 190 is transmitted to a circuit 193, this circuit also receiving via a line 194 the M-signal pulsed through the switch 156. The signals are subtracted in the circuit 193 so that a pulsed output signal from the circuit 193 represents an X minus M signal, which corresponds to the roll resistance acting on the wheel 3. Said pulsed output signal is transmitted to an integrator 195 for integration. The output signal of the integrator 195 is transmitted to a divider circuit 196, to be divided there by a signal value transmitted via a line 197, and integrated during the same time and distance by the integrator 165. On the output of the divider circuit 196 there is obtained a signal representing an average value for the roll resistance during the measuring sequence, said signal being transmitted to the recorder 140 via an A/D-converter 198.

As for the M-signal, conversion from analog to digital signal form only takes place in the presence of a control signal from the comparator 175 to the A/D converter 198 via a line 199. When such conversion to digital form is carried out, a control signal is transmitted via a line 186 to the recorder 140 for triggering registration. Similar to the integrators 160 and 165, the integrator 195 obtains a zeroing signal from the delaying circuit of the counter 180 via a line 178, the integrator 195 assuming the starting position for the formation of a new average value.

The chart recorder 140 is suitably of the type which, on a single information carrier, e.g., a strip chart or tape, can record, on the one hand, the momentary friction value over the measuring distance in analog form, and on the other hand average friction values and average roll resistance values at each third of the distance in digital form.

With the measuring apparatus according to the invention there is thus provided registration over the whole measuring distance of the momentary friction value on an indicating instrument and in a durable form on the strip. If considered suitable, different recorders can be used for the analog and digital representation.

Other partial measuring distances or the whole distance can moreover be selected as a basis for average value calculation. Since the measurement of the roll resistance is in certain cases of less interest than the friction measurement, the measuring apparatus can, within the scope of the invention idea, be simplified so that the measuring apparatus only renders the momentary friction value in analog form and the average friction value in digital form.

When the whole of the selected distance has been travelled, the wheel is automatically retracted to the inactive position, and the recorder drive motor is similarly automatically shut off. The driver thus does not need to take any action himself to stop measurement and neither does he need to read off, register or calculate reference values, these being recorded on the information carrier of the recorder at the end of the measuring distance.

Figure 4:
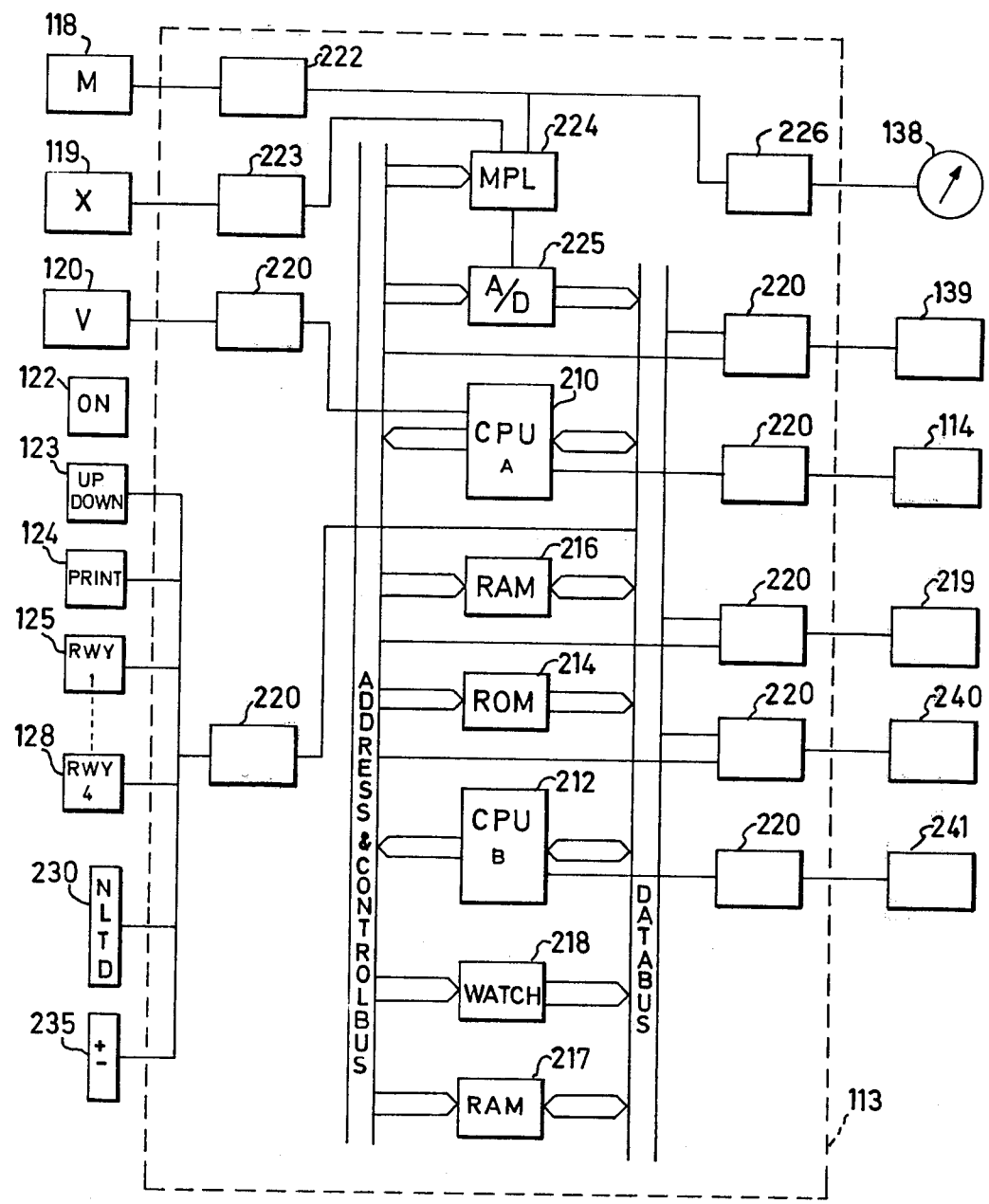
FIG. 4 shows a block diagram of an electric system based upon micro computer technology, and FIG. 5 exemplifies a strip chart showing the result of a measuring sequence.

In accordance with the FIG. 4 the measuring apparatus can also comprise a more technically advanced embodiment of the electrical system, the central block 113 being built up using so-called micro processor techniques. A micro processor which deals with the signal values in digital form thereby comprises two central processing units 210, 212, which in the continuation are called CPU-A 210 and CPU-B 212. The CPU-A 210 making arithmetical calculations and the CPU-B 212 taking care of feeding data to the registration block. Both processing units 210, 212 are controlled by programs stored in a read memory, called ROM 214, said programs also controlling two registrations units, of random access memory type, which units are called RAM 216 and RAM 217. The RAM-memory 216 is intended to store data from a clock unit, called WATCH 218, for later output of data defining time and day on a display unit 219 and a recorder 240. The signal lamps in the lamp unit 139 are arranged to be supplied with current in order to indicate certain conditions achieved during a measurement.

The signals between the units incorporated in the micro processor are separated into signals representing a certain address, signals having control functions and signals relating to data. Said signals are transmitted via line collected into bundles, said bundles being represented in FIG. 4 as ADDRESS CONTROL BUS and DATABUS, respectively. The arrows between the units of the micro processor and the BUS-lines indicate whether the units receive or send address- or datasignals, respectively.

Figure 5:
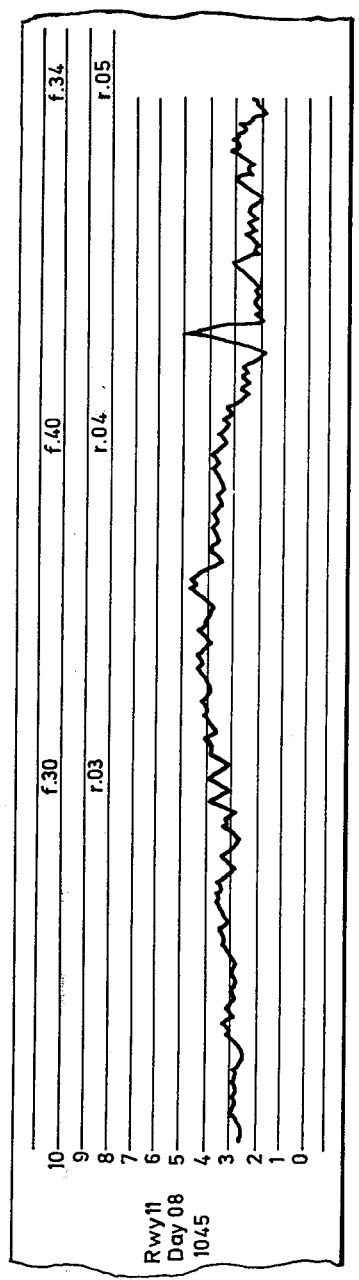

In the central block 113 there is also included a number of matching circuits 220, which for digital signal processing normally are called Interface. Each such matching circuit 220 transforms an in-signal to a proper out-signal for processing in a following unit. Also the analog signals M and X from the transducers 118, 119 are adapted in the blocks 222 and 223, respectively, for amplification and filtering before they are fed to a multiplexing unit, called MPL 224. Depending on the presence or non-presence of external control signals, the MPL 224 alternatingly transmit M-signals or X-signals to an A/D-converter 225, where analog signals are converted into digital signals. The analog M-signal from the transducer 118 is via an amplifier 226 fed to a pointer type instrument 138 for indication of the momentary frictional value. Display of the momentary frictional value in the shape of a graph on a strip is in this case preferably achieved by means of the recorder 240, which, on the basis of received digital signals, plots a graph on the strip. In addition to said graph, there is also indicated on the strip a digital information about the mean frictional value over for instance each third of the measuring distance, as has previously been described in connection with FIG. 3. In FIG. 5 there is shown a sample of such a strip. The mean frictional value over each distance segment is preceded by the letter "f", and the values preceded by the letter "r" indicate the mean roll resistance values. At the beginning of the frictional graph there is indicated the number of the selected measuring distance, as well as the day and the time.

The print-out of such a strip is controlled by programs stored in the ROM-memory 214. Depending on which controls are activated, different, more or less complex programs are executed. When selecting for the measurement the routine described in connection with FIG. 2 it is thus feasible to first activate one of the RWY -switches 125-128. In this way a program is selected that registers the runway number, the day and the time on the strip. A consequent activation of the switch DOWN 123 causes the measuring wheel 3 to be lowered into measuring position, and activation also of the switch PRINT 124 then causes a calculation program stored in the ROM-memory 214 to be executed. On the basis of in-signals M, X and V from the transducers 118,119 and 120 the CPU-A 210 executes, using digital signal values, the arithmetic operations earlier referred to in connection with the analog signal processing in FIG. 3. The resulting signal values are stored in the RAM-memory 216, the feed-out from which to the recorder 240 is controlled primarily by CPU-B 212. From CPU-B 212 also the motor 241 of the recorder 240 is controlled by digital signals, the levels of said signals being proportional to the level of the signal from the transducer 120.

CPU-A 210 is also directly connected to the block 114, which controls the movement of the measuring wheel 3 to and from its measuring position.

(In a practical embodiment of the arrangement in FIG. 4, a Nippon Hamlin type CSP-2 recorder has been used as recorder 240. As central processing units CPU-A 210 and CPU-B 212 were used units from National Semiconductor called ISP-8A/600N, said units normally being referred to and known under the designation SC/MP).

The display-unit 219, which can be of the LED-type (LED=Light Emitting Diode), can by means of a control, in this case a thumb wheel selector 230 having four positions N, L, T and D, respectively, be made to display the signal values stored in the RAM-memories and representing the number and the length of the alternative measuring distances, as well as the time and the day. In order to have the number of a certain measuring distance displayed it is, in addition to setting the thumb wheel selector 230 in a position for indication of the number, also necessary to press the proper RWY-button 125-128. A corresponding procedure has to be adopted for displaying the selected length of a certain measuring distance, and also for displaying the time and the date. By activating a switch 235 when either of said data is presented on the display unit 219, the value of said variable stored in the RAM-memories 216,217 can be changed.

In the embodiments described above, only electronic circuits well known to the man of the art have been used, and therefore the description of the arrangement according to the invention has been restricted to what is shown on the drawing. As to the embodiment shown in FIG. 4, a man of the art who knows how to program micro processors, can easily arrive at an electronic unit 113 capable of doing the work required. The possibility of choosing between different preset measuring distances makes the measuring apparatus particularly advantageous for use at airports. Integration of the apparatus into an automobile, together with the simple actions required for carrying out measurement further make it possible to carry out reliable measurements with staff who are not especially trained.

The invention is not limited to the embodiment example described hereinabove but can within the framework of the invention and the following claims be modified into a variety of embodiments. It is thus obvious that the constructional solutions for the components of the arrangement only constitute descriptive examples and corresponding practical solutions can be varied in many different ways.

What is claimed is:

1. An apparatus incorporated in a wheeled motor vehicle for measuring and indicating coefficient of friction values for driving and braking vehicles on a substructure, said measuring apparatus comprising:
   at least one control panel, arranged in the vehicle, with a plurality of control means for selection and control of a measuring sequence;

at least one measuring wheel pivotally mounted in the vehicle so as to be raisable and lowerable to engage and disengage said substructure, said wheel engaging the substructure at least during said measuring sequence, and said wheel rotating when engaged with said substructure with an amount of slip relative the speed of the wheeled vehicle;

at least one force measuring transducer mounted to said vehicle including means for sensing the forces and/or torque acting on the measuring wheel and generating signals corresponding thereto;

at least one vehicle speed measuring transducer mounted to the vehicle including means for sensing the speed of the vehicle and generating a pulsed signal corresponding thereto;

at least one electronic unit including a memory for storing a plurality of preset measuring distances, said unit being mounted to the vehicle, and further including means for receiving and processing signals generated by said force measuring transducers and said speed measuring transducers, and in response thereto transmitting output signals to a plurality of instruments displaying the measuring results; and a plurality of controls mounted to said vehicle including means for selecting measuring distances of different length, each control triggering, when actuated, the switching in circuit of a first signal value preselected to represent the measuring distance in question in said memory, said electronic unit including means for comparing said first signal with a second signal value generated by summing up signal pulses generated by said vehicle speed transducer and representing the distance travelled by the vehicle during said measuring sequence, and wherein said electronic unit also includes means for triggering discontinuation of said measuring sequence when said first and second signal values are equal.

2. An apparatus as claimed in claim 1, wherein said electronic unit comprises at least a second memory for storing data relating to date, time and runway numbers corresponding to the preselected distances, said apparatus further including a registration block for receiving said data and for displaying said data on an information carrier after activation of controls for selection of runway number and for lowering the measuring wheel to engage the substructure.

3. An apparatus as claimed in claim 2, further comprising means for measuring roll resistance and a chart repeater and wherein said electronic unit may be programmed to produce signals, when said first and second signals values are equal, representing average values calculated in the unit of the coefficient of friction and roll resistance over the measuring distance travelled, said signals being applied to said chart recorder for enduring registration of said average values on an information carrier.

4. An apparatus as claimed in claim 3, in which the electronic unit triggers a signal to a circuit, controlling the pivotal movement of the measurement wheel, whereby said circuit activates servo means to disengage the measuring wheel from the substructure upon the discontinuance of the measuring sequence.

5. An apparatus as claimed in claim 3, wherein the electronic unit is programmed to produce signal values representing the average friction coefficient and roll resistance calculated in the unit, said signal values pertaining to the measuring distance travelled when the vehicle has travelled a predetermined portion of the measuring distance.

6. An apparatus as claimed in claim 5, wherein said values are registered in analog form.

7. An apparatus as claimed in claim 5, wherein said values are registered in digital form.

8. An apparatus as claimed in claim 3, wherein said electronic unit comprises a preprogrammed micro computer dealing with the signal values in digital form, said micro computer comprising at least one control processing unit and at least one memory of the random access memory type.

9. An apparatus as claimed in claim 2, wherein all operating means are arranged in an operating panel and wherein the operating panel and registration means are included in a common unit within the passenger compartment of the vehicle.

* * * * *